(12) United States Patent
Kouno et al.

(10) Patent No.: US 12,264,311 B2
(45) Date of Patent: Apr. 1, 2025

(54) METHOD FOR ISOLATING NUCLEIC ACID, NUCLEIC ACID ISOLATION KIT, AND INSPECTION CHIP

(71) Applicants: SEKISUI CHEMICAL CO., LTD., Osaka (JP); SEKISUI MEDICAL CO., LTD., Tokyo (JP)

(72) Inventors: Takamasa Kouno, Osaka (JP); Nobuhiko Inui, Saitama (JP); Tsutomu Nakamura, Osaka (JP); Tomoya Sasaki, Saitama (JP); Sou Yamaguchi, Tokyo (JP); Katsura Uchida, Tokyo (JP)

(73) Assignees: SEKISUI CHEMICAL CO., LTD., Osaka (JP); SEKISUI MEDICAL CO., LTD., Tokyo (JP)

( * ) Notice: Subject to any disclaimer, the term of this patent is extended or adjusted under 35 U.S.C. 154(b) by 932 days.

(21) Appl. No.: 17/422,602

(22) PCT Filed: Jan. 17, 2020

(86) PCT No.: PCT/JP2020/001461
§ 371 (c)(1),
(2) Date: Jul. 13, 2021

(87) PCT Pub. No.: WO2020/153248
PCT Pub. Date: Jul. 30, 2020

(65) Prior Publication Data
US 2022/0090048 A1    Mar. 24, 2022

(30) Foreign Application Priority Data

| Jan. 25, 2019 | (JP) | 2019-011186 |
| Feb. 20, 2019 | (JP) | 2019-028014 |
| Mar. 29, 2019 | (JP) | 2019-067480 |
| Oct. 4, 2019 | (JP) | 2019-183676 |

(51) Int. Cl.
*C12N 15/10* (2006.01)
*C12Q 1/6806* (2018.01)

(52) U.S. Cl.
CPC ....... *C12N 15/1003* (2013.01); *C12Q 1/6806* (2013.01)

(58) Field of Classification Search
CPC . C12N 15/1003; C12N 15/101; C12Q 1/6806
See application file for complete search history.

(56) References Cited

U.S. PATENT DOCUMENTS

| 2001/0018513 A1 | 8/2001 | Baker |
| 2003/0008320 A1 | 1/2003 | Baker |
| 2003/0054395 A1 | 3/2003 | Baker |
| 2003/0130499 A1 | 7/2003 | Baker |
| 2006/0024712 A1 | 2/2006 | Baker et al. |
| 2006/0105372 A1 | 5/2006 | Bair et al. |
| 2007/0231892 A1 | 10/2007 | Baker |
| 2007/0292884 A1* | 12/2007 | McGill ................ C12Q 1/6806 435/91.2 |
| 2008/0305528 A1 | 12/2008 | Baker |
| 2009/0306359 A1 | 12/2009 | Hillebrand et al. |
| 2012/0196944 A1 | 8/2012 | Baker |
| 2012/0197009 A1 | 8/2012 | Baker |
| 2012/0245337 A1 | 9/2012 | Fabis et al. |
| 2013/0158247 A1 | 6/2013 | Fabis et al. |
| 2013/0203150 A1* | 8/2013 | Pullela ................ C12N 15/1006 435/270 |
| 2013/0338245 A1 | 12/2013 | Baker |
| 2014/0087366 A1* | 3/2014 | Srinivasan ........... C12Q 1/6806 435/6.12 |

(Continued)

FOREIGN PATENT DOCUMENTS

| CN | 102115711 | 7/2011 |
| CN | 102264901 | 11/2011 |

(Continued)

OTHER PUBLICATIONS

Vandeventer, P. E.; et al. "Multiphasic DNA Adsorption to Silica Surfaces under Varying Buffer, pH, and Ionic Strength Conditions" 2012, Journal of Physical Chemistry B, vol. 116, pp. 5661-5670. (Year: 2012).*

Kornblatt, M. J.; et al. "The effects of sodium perchlorate on rabbit muscle enolase: Spectral characterization of the monomer" 1996, European Journal of Biochemistry, vol. 236, pp. 78-84. (Year: 1996).*

Fuguet, E.; et al. "Critical evaluation of buffering solutions for pKa determination by capillary electrophoresis" 2008, Electrophoresis, vol. 29, pp. 2841-2851. (Year: 2008).*

(Continued)

*Primary Examiner* — Eric Olson
*Assistant Examiner* — Benjamin M Brandsen
(74) *Attorney, Agent, or Firm* — Wenderoth, Lind & Ponack, L.L.P.

(57) ABSTRACT

Provided is a nucleic acid isolation method whereby it becomes possible to extract a nucleic acid in a simple manner without the need to use an alcohol. A nucleic acid isolation method, comprising the steps of: mixing a specimen containing a nucleic acid with an extraction solution to disperse the nucleic acid in the extraction solution; bringing the extraction solution containing the nucleic acid into contact with an anionic adsorbent; bringing a washing solution into contact with the anionic adsorbent; and bringing a collection solution into contact with the anionic adsorbent, the extraction solution containing a protein denaturant, the washing solution containing a basic compound and having a pH value equal to or less than a pKa value of a conjugate acid of the basic compound, and the collection solution having a pH value equal to or more than the pKa value of the conjugate acid of the basic compound.

7 Claims, 3 Drawing Sheets

(56) References Cited

U.S. PATENT DOCUMENTS

| | | | |
|---|---|---|---|
| 2014/0134718 A1* | 5/2014 | Hiesinger | C12N 15/1017 536/25.4 |
| 2018/0133710 A1 | 5/2018 | Hillebrand et al. | |
| 2018/0148712 A1 | 5/2018 | Hillebrand et al. | |
| 2018/0148766 A1 | 5/2018 | Hillebrand et al. | |
| 2019/0345480 A1 | 11/2019 | Bair et al. | |
| 2023/0183674 A1* | 6/2023 | Yamaguchi | C12Q 1/6806 536/25.41 |

FOREIGN PATENT DOCUMENTS

| | | | |
|---|---|---|---|
| CN | 206375900 | 8/2017 | |
| JP | 2004-501054 | 1/2004 | |
| JP | 2008-518618 | 6/2008 | |
| JP | 2012-513385 | 6/2012 | |
| JP | 2018-524017 | 8/2018 | |
| WO | WO-2009129524 A2 * | 10/2009 | C12N 15/1003 |
| WO | WO 2010/038778 | 4/2010 | |

OTHER PUBLICATIONS

Merck Index entry of Triethylenediamine (accessed Oct. 15, 2024). (Year: 2024).*

Khalili, F.; et al. "pKa Values of Some Piperazines at (298, 303, 313, and 323) K" 2009, Journal of Chemical and Engineering Data, vol. 54, pp. 2914-2917. (Year: 2009).*

Extended European Search Report issued Sep. 21, 2022, in corresponding European Patent Application No. 20745625.2, 9 pages.

Hønsvall et al., "Washed Away; How Not to Lose Your RNA during Isolation", Journal of Biomolecular Techniques, 2017, vol. 28, No. 2, pp. 75-79, 6 pages.

Katevatis et al., "Low concentration DAN extraction and recovery using a silica solid phase", PLOS ONE, 2017, vol. 12, No. 5, e0176848, pp. 1-14, 14 pages.

Ali et al., "Current Nucleic Acid Extraction Methods and Their Implications to Point-of-Care Diagnostics", Biomed Research International, 2017, vol. 2017, pp. 1-13, 14 pages.

Jue et al., "Two-phase wash to solve the ubiquitous contaminant-carryover problem in commercial nucleic-acid extraction kits", Scientific Reports, 2020, vol. 10, No. 1, pp. 1-16, 16 pages.

International Preliminary Report on Patentability and Written Opinion issued Jul. 27, 2021 in corresponding International (PCT) Patent Application No. PCT/JP2020/001461.

International Search Report issued Apr. 7, 2020 in International (PCT) Application No. PCT/JP2020/001461.

Office Action issued Oct. 11, 2022 in corresponding Singapore Patent Application No. 11202104814X, 8 pages.

* cited by examiner

[FIG. 1.]
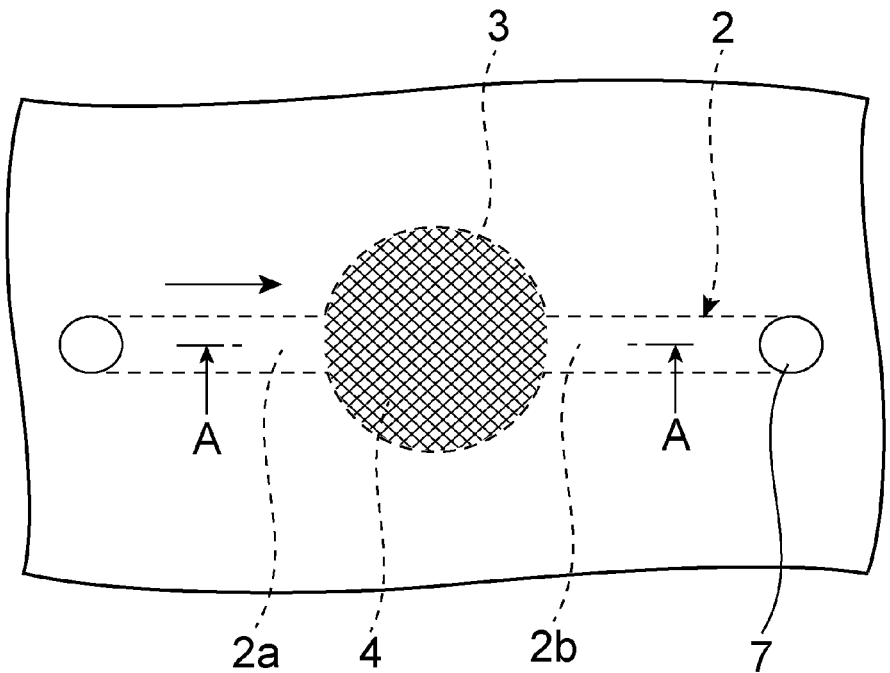
[FIG. 2.]
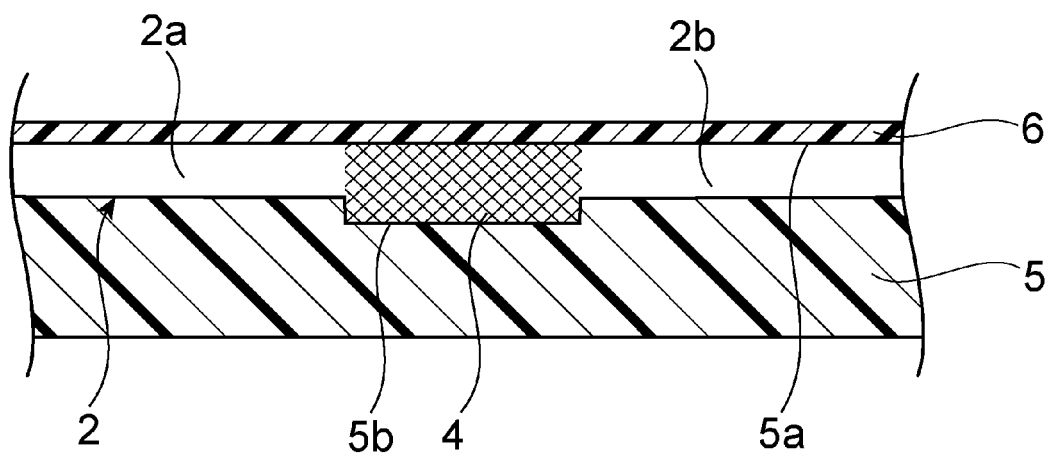

[FIG. 3.]
(a)
(b)
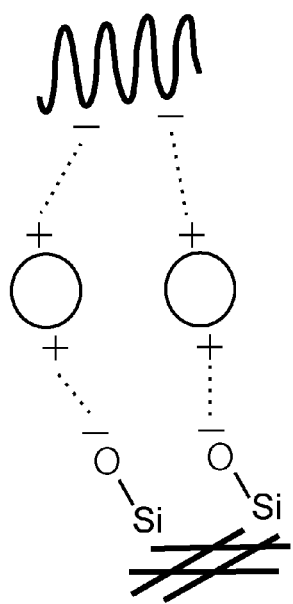
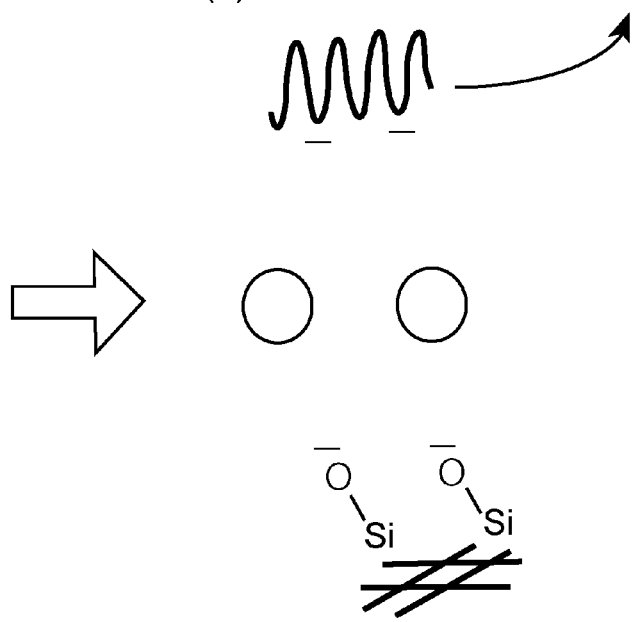

[FIG. 4.]
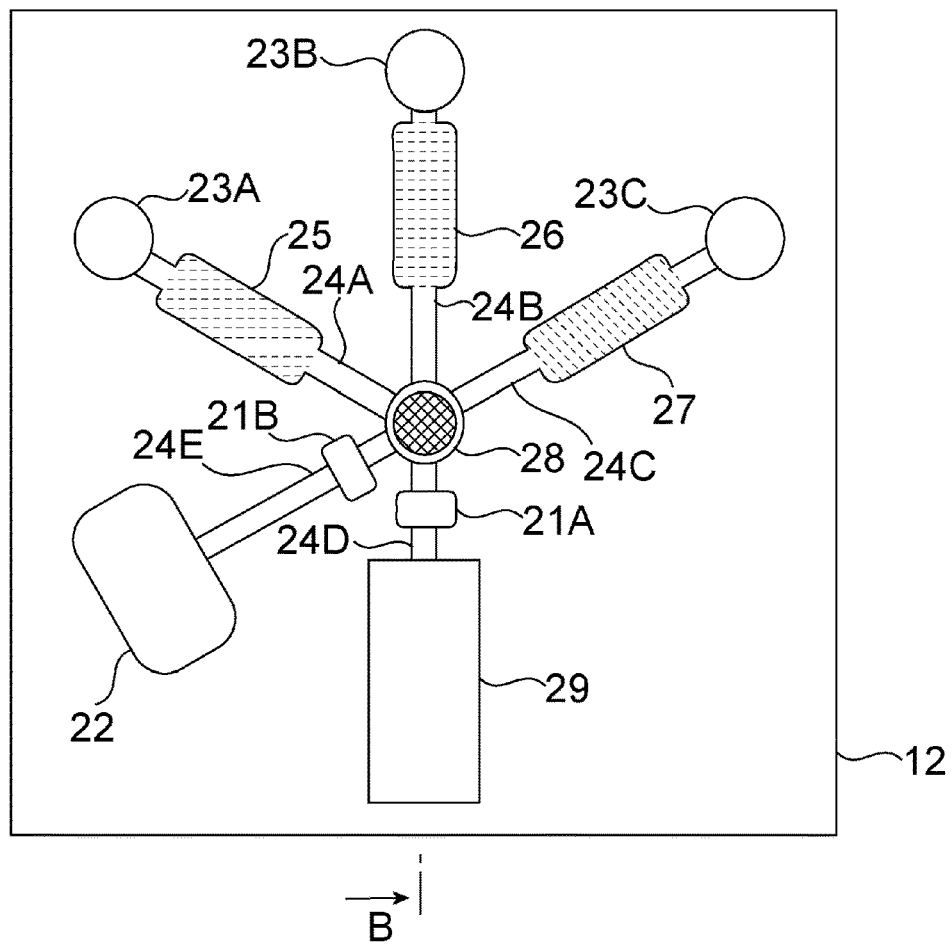
[FIG. 5.]
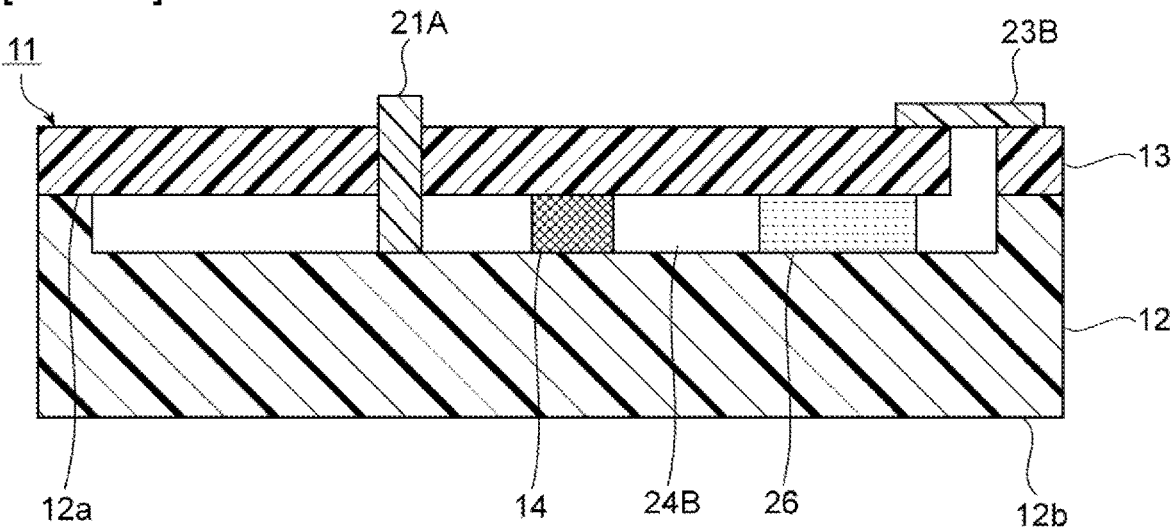

METHOD FOR ISOLATING NUCLEIC ACID, NUCLEIC ACID ISOLATION KIT, AND INSPECTION CHIP

TECHNICAL FIELD

The present invention relates to a nucleic acid isolation method, a nucleic acid isolation kit and a test chip.

BACKGROUND ART

Heretofore, as a method for isolating a nucleic acid, e.g., RNA and DNA, contained in a virus or a cell, a method is known in which a nucleic acid extracted from a virus or a cell is filtered through a filter and then impurities, e.g., a salt, adhered onto the filter are washed together with the nucleic acid. As a washing solution to be used for the washing, an alcohol, e.g., ethanol, has been generally used.

For example, Patent Document 1 discloses a method in which a nucleic acid is bonded to a material which is placed vertically in a pipette chip and to which a nucleic acid can be bonded and then the material is washed with a washing buffer. In Patent Document 1, after the washing with the washing buffer, a drying step is carried out and then the nucleic acid is isolated with an eluent. In Patent Document 1, as the washing buffer, an alcohol, e.g., ethanol, is used.

RELATED ART DOCUMENT

Patent Document

Patent Document 1: JP 2018-524017 T

SUMMARY OF THE INVENTION

Problems to be Solved by the Invention

However, when an alcohol is used as a washing solution as disclosed in Patent Document 1, there is a problem that the alcohol is likely to volatilize during the storage of the washing solution. Furthermore, when an alcohol is used as the washing solution, it is needed to further provide a drying step as disclosed in Patent Document 1, and therefore there is a problem that the process becomes complicated. When a drying step is not provided, if an alcohol is used in a test or an analysis in a later step, a reaction such as an enzymatic reaction may be inhibited.

The object of the present invention is to provide a nucleic acid isolation method, a nucleic acid isolation kit and a test chip, whereby it becomes possible to extract a nucleic acid in a simple manner without the need to use an alcohol.

Means for Solving the Problems

In a broad aspect of the nucleic acid isolation method according to the present invention, the method comprises the steps of:
  mixing a specimen containing a nucleic acid with an extraction solution to disperse the nucleic acid in the extraction solution;
  bringing the extraction solution containing the nucleic acid into contact with an anionic adsorbent;
  bringing a washing solution into contact with the anionic adsorbent; and
  bringing a collection solution into contact with the anionic adsorbent,
wherein:
  the extraction solution contains a protein denaturant;
  the washing solution contains a basic compound and has a pH value equal to or less than a pKa value of a conjugate acid of the basic compound; and
  the collection solution has a pH value equal to or more than the pKa value of the conjugate acid of the basic compound.

In a specific aspect of the nucleic acid isolation method according to the present invention, the extraction solution further contains a metal cation having a valency of 2 or more.

In another broad aspect of the nucleic acid isolation method according to the present invention, the method comprises the steps of:
  mixing a specimen containing a nucleic acid with an extraction solution to disperse the nucleic acid in the extraction solution;
  bringing the extraction solution containing the nucleic acid into contact with an anionic adsorbent; and
  bringing a collection solution into contact with the anionic adsorbent,
wherein:
  the extraction solution contains a protein denaturant and a basic compound, and has a pH value equal to or less than a pKa value of a conjugate acid of the basic compound; and
  the collection solution has a pH value equal to or more than the pKa value of the conjugate acid of the basic compound.

In another specific aspect of the nucleic acid isolation method according to the present invention, the pKa value of the conjugate acid of the basic compound is 4 or more and 6 or less.

In still another specific aspect of the nucleic acid isolation method according to the present invention, the basic compound has an amino group.

In still another specific aspect of the nucleic acid isolation method according to the present invention, the extraction solution further contains a zwitterionic compound.

In still another specific aspect of the nucleic acid isolation method according to the present invention, a step of bringing a solution containing an alcohol into contact with the anionic adsorbent is not included.

In a broad aspect of the nucleic acid isolation kit according to the present invention, the kit comprises:
  an extraction solution;
  a washing solution;
  a collection solution; and
  an anionic adsorbent,
wherein:
  the extraction solution contains a protein denaturant;
  the washing solution contains a basic compound and has a pH value equal to or less than a pKa value of a conjugate acid of the basic compound; and
  the collection solution has a pH value equal to or more than the pKa value of the conjugate acid of the basic compound.

In a specific aspect of the nucleic acid isolation kit according to the present invention, the extraction solution further contains a metal cation having a valency of 2 or more.

In another broad aspect of the nucleic acid isolation kit according to the present invention, the kit comprises:
  an extraction solution;
  a collection solution; and
  an anionic adsorbent, wherein:
the extraction solution contains a protein denaturant and a basic compound and has a pH value equal to or less than a pKa value of a conjugate acid of the basic compound; and
the collection solution has a pH value equal to or more than the pKa value of the conjugate acid of the basic compound.

In a broad aspect of the test chip according to the present invention, the test chip comprises:
an extraction solution holding section in which an extraction solution containing a nucleic acid is held;
a washing solution holding section in which a washing solution is held;
a collection solution holding section in which a collection solution is held;
a collection section containing an anionic adsorbent; and
a nucleic acid analysis section,
wherein:
the extraction solution contains a protein denaturant;
the washing solution contains a basic compound and has a pH value equal to or less than a pKa value of a conjugate acid of the basic compound; and
the collection solution has a pH value equal to or more than the pKa value of the conjugate acid of the basic compound.

In a specific aspect of the test chip according to the present invention, the extraction solution further contains a metal cation having a valency of 2 or more.

In another broad aspect of the test chip according to the present invention, the test chip comprises:
an extraction solution holding section in which an extraction solution containing a nucleic acid is held;
a collection solution holding section in which a collection solution is held;
a collection section containing an anionic adsorbent; and
a nucleic acid analysis section,
wherein:
the extraction solution contains a protein denaturant and a basic compound and has a pH value equal to or less than a pKa value of a conjugate acid of the basic compound; and
the collection solution has a pH value equal to or more than the pKa value of the conjugate acid of the basic compound.

Effect of the Invention

According to the present invention, it becomes possible to provide a nucleic acid isolation method, a nucleic acid isolation kit and a test chip whereby it becomes possible to extract a nucleic acid in a simple manner without the need to use an alcohol.

BRIEF DESCRIPTION OF DRAWINGS

FIG. 1 is a schematic plan view showing a chip used in a nucleic acid collection method according to a first embodiment of the present invention.
FIG. 2 is a schematic sectional view of a part taken along line A-A in FIG. 1.
FIG. 3(a) is a schematic view illustrating a state where a nucleic acid is adsorbed onto an anionic adsorbent, and FIG. 3(b) is a schematic view illustrating a state where the nucleic acid is isolated from the anionic adsorbent, in the nucleic acid isolation method according to the present invention.
FIG. 4 is a schematic plan view showing one example of a flow path structure in a test chip according to a first embodiment of the present invention.
FIG. 5 is a schematic sectional view of a part taken along line B-B in FIG. 4.

MODES FOR CARRYING OUT THE INVENTION

Hereinbelow, the present invention is described in detail.
[Nucleic Acid Isolation Method]
The present invention relates to a nucleic acid isolation method. Hereinbelow, the present invention is described clearly by explaining specific embodiments of the present invention.
(Nucleic Acid Isolation Method According to First Embodiment)
The nucleic acid isolation method according to a first embodiment of the present invention comprises the steps of:
mixing a specimen containing a nucleic acid with an extraction solution to disperse the nucleic acid in the extraction solution;
bringing the extraction solution containing the nucleic acid into contact with an anionic adsorbent;
bringing a washing solution into contact with the anionic adsorbent; and
bringing a collection solution into contact with the anionic adsorbent. The extraction solution contains a protein denaturant. The washing solution contains a basic compound and has a pH value equal to or less than the pKa value of a conjugate acid of a basic compound. The collection solution has a pH value equal to or more than the pKa value of the conjugate acid of a basic compound. Hereinbelow, the steps are explained.
(Extraction Step)
The nucleic acid isolation method according to a first embodiment of the present invention includes a step of mixing a specimen containing a nucleic acid with an extraction solution to disperse the nucleic acid in the extraction solution. This step is referred to as an "extraction step" and is explained hereinafter.
As the specimen containing a nucleic acid, a biological specimen containing a nucleic acid such as DNA and RNA. Examples of the biological specimen include a virus, a cell, blood, a tissue fluid and feces. The specimen containing a nucleic acid may also be a specimen containing a nucleic acid occurring in the environment, such as soil, sea water and river water, and is not particularly limited.
The extraction solution contains a protein denaturant. The protein denaturant has a function to interact with a protein to disrupt the higher structure of the protein and dissolve a nucleic acid in the extraction solution. As the protein denaturant, a surfactant, a reducing agent, a guanidine derivative, thiourea, urea, a salt of any one of these components or the like can be used. As the surfactant, sodium dodecyl sulfate (SDS), polyoxyethylene sorbitan monolaurate (Tween20) or the like can be used. As the reducing agent, 2-mercaptoethanol, dithiothreitol (DTT) or the like can be used. As the salt, a salt such as guanidine hydrochloride can be used. These protein denaturants may be used singly, or two or more of them may be used in combination.
The concentration of the protein denaturant in the extraction solution is not particularly limited, and is preferably 2 mol/L or more, more preferably 4 mol/L or more, still more preferably 8 mol/L or more, and is also preferably 10 mol/L or less. By adjusting the concentration of the protein denaturant to a value falling within the above-mentioned range, it becomes possible to extract the nucleic acid more reliably. When two or more types of protein denaturants are used, it is preferred that the total concentration of the protein denaturants falls within the above-mentioned range.

It is preferred that the extraction solution contains a zwitterionic compound as the protein denaturant.

When a nonionic surfactant or the like is used as the protein denaturant in the extraction solution, although the collection rate of the nucleic acid can be improved, a reaction such as PCR may be inhibited in a test or an analysis in a later step. Therefore, the extraction of the nucleic acid within a short time may become difficult to achieve as a result of reducing the amount of the nonionic surfactant or additionally providing a washing step. On the other hand, when the protein denaturant like a nonionic surfactant is not used, the collection rate of the nucleic acid may not be increased sufficiently.

When the extraction solution contains a zwitterionic compound, a cationic functional group in a protein (e.g., histone) contained in the specimen containing the nucleic acid interacts with an anionic functional group in the zwitterionic compound upon the contact of the specimen with the zwitterionic compound. As a result, the bond between the protein and the nucleic acid can be cleaved and the nucleic acid can be extracted efficiently. Therefore, it becomes possible to collect the nucleic acid more efficiently in a later step.

A zwitterionic compound has also a cationic functional group, and therefore can impart a charge-dependent bonding point in the nucleic acid. More specifically, an anionic functional group in the zwitterionic compound can also form a bond together with a base in the nucleic acid, and therefore it becomes possible to prevent the nucleic acid from becoming electrically neutral by the action of the cationic functional group in the zwitterionic compound. When a nucleic acid becomes electrically neutral, the coagulation among molecules of the nucleic acid proceeds, resulting in the decrease in efficiency of a reaction such as PCR. In contrast, when a zwitterionic compound is used, it becomes possible to prevent the nucleic acid from becoming electrically neutral by the action of the zwitterionic compound, and therefore analysis accuracy can be further improved in an analysis which is required to be carried out within a short time, e.g., PCR.

It is preferred that the zwitterionic compound does not have a surface activity. The wording "a component does not have a surface activity" as used herein refers to a fact that the HLB value of the component is 0 to 6 or 13 to 20 as measured by a Griffin method. In this case, the inhibition of a reaction such as PCR can be prevented more reliably and the nucleic acid can be extracted within a shorter time in a test or an analysis in a later step.

The zwitterionic compound is not particularly limited. As the zwitterionic compound, an amino acid or an amino acid derivative, a nucleotide, or a polymer having a repeating structural unit derived from any one of these monomers can be used. Among these compounds, an amino acid or an amino acid derivative is preferred as the zwitterionic compound. In this case, it becomes possible to collect the nucleic acid more efficiently within a shorter time.

The amino acid or the amino acid derivative is not particularly limited. For example, a naturally occurring amino acid such as glycine, acetylcysteine, a D-amino acid, a diamine, a ω-amino acid, a β-amino acid, a γ-amino acid, an aminophosphonic acid, and a polymer having a repeating structural unit derived from any one of these monomers can be used.

Examples of the commercially available zwitterionic compound include LIPIDURE (NOF Corporation) and PNA (Cosmo Bio Co. Ltd.).

These zwitterionic compounds may be used singly, or two or more of them may be used in combination.

When the extraction solution contains a zwitterionic compound, the concentration of the zwitterionic compound in the extraction solution is not particularly limited, and is preferably 0.5 mol/L or more, more preferably 1.0 mol/L or more, and is also preferably 10.0 mol/L or less, more preferably 8.0 mol/L or less. When the concentration of the zwitterionic compound in the nucleic acid extraction solution falls within the above-mentioned range, it becomes possible to collect the nucleic acid more efficiently within a shorter time.

The extraction solution preferably contains a metal cation having a valency of 2 or more. Examples of the metal cation having a valency of 2 or more include a calcium ion and a magnesium ion. When the extraction solution contains a metal cation having a valency of 2 or more, the collection rate of the nucleic acid can be further improved.

When the extraction solution contains a metal cation having a valency of 2 or more, the metal cation binds to the negatively charged nucleic acid via an ionic bond upon the addition of the specimen containing the nucleic acid to the extraction solution. Upon the contact of the extraction solution from which the nucleic acid having the metal cation bonded thereto via an ionic bond has been extracted with the anionic adsorbent, the metal cation binds to the anionic adsorbent via an ionic bond, as shown in FIG. 3(a). As a result, the nucleic acid can be adsorbed onto the anionic adsorbent through the metal cation.

The extraction solution may further contain a co-precipitant. Examples of the co-precipitant include tRNA, polyadenine, an acrylamide polymer and glycogen. When the extraction solution further contains the co-precipitant, it becomes possible to allow the nucleic acid to be adsorbed onto the anionic adsorbent more efficiently.

The metal cation cannot inhibit the extraction of the nucleic acid even when added in the extraction solution previously. Therefore, any complicated step is not necessary for the extraction of the nucleic acid.

When the extraction solution contains a metal cation having a valency of 2 or more, the concentration of the metal cation having a valency of 2 or more in the extraction solution is not particularly limited, and is preferably 0.5 mol/L or more, more preferably 1.0 mol/L or more, and is also preferably 6.0 mol/L or less, more preferably 5.0 mol/L or less. When the concentration of the metal cation having a valency of 2 or more in the extraction solution falls within the above-mentioned range, it becomes possible to collect the nucleic acid more efficiently within a shorter time.

In addition to the above-mentioned components, the extraction solution may further contain other components such as a pH modifier and a stabilizing agent.

(Adsorption Step)

Subsequently, the nucleic acid isolation method according to the first embodiment of the present invention includes a step of bringing the extraction solution containing the nucleic acid into contact with an anionic adsorbent. This step is referred to as an "adsorption step" and is explained hereinafter.

FIG. 1 is a schematic plan view showing a chip used in the nucleic acid isolation method according to the first embodiment of the present invention. FIG. 2 is a schematic sectional view of a part taken along line A-A in FIG. 1. In the following explanation, the isolation of the nucleic acid is carried out using a microfluidic device equipped with a chip 1. The isolation of the nucleic acid may also be carried out using other container. The device to be used for the isolation is not particularly limited.

As shown in FIGS. 1 and 2, the chip 1 is equipped with a flow path 2 through which a fluid can be fed. In the middle of the flow path 2, a collection section 3 is provided. Therefore, the flow path 2 has an upstream-side flow path 2a which is provided on the upstream side of the collection section 3 and a downstream-side flow path 2b which is provided on the downstream side of the collection section 3. The chip 1 is provided with a plate-like substrate 5 and a cover member 6. The cover member 6 is arranged on a main surface 5a of the substrate 5 so as to close an opening of a depressed part 5b in the substrate 5. As a result, the upstream-side flow path 2a, the collection section 3 and the downstream-side flow path 2b are formed. The material constituting the substrate 5 is not particularly limited. For example, a synthetic resin, a rubber or a metal can be used. The cover member 6 can be formed from a material having flexibility, such as a resin film.

Anionic Adsorbent;

In the collection section 3, an anionic adsorbent 4 which can support the nucleic acid thereon and can help to collect the nucleic acid is arranged. The anionic adsorbent is a supporting body for supporting the nucleic acid thereon.

The form of the anionic adsorbent 4 is not particularly limited. For example, the anionic adsorbent 4 can be used in the form of a membrane, a filter, a plate, a fibrous material, a tube, particles or a porous body. The form of the anionic adsorbent 4 is preferably a fiber, particles, or a porous body.

The anionic adsorbent 4 can be formed from, but is not particularly limited to, a silicon compound, a phosphate mineral, a silicate mineral, an aliminosilicate mineral or the like. Examples of the silicon compound include silica and glass. An example of the phosphate mineral is hydroxyapatite. Examples of the silicate mineral include talc and montmorillonite. An example of the aluminosilicate mineral is zeolite. These components may be used singly, or two or more of them may be used in combination.

The anionic adsorbent 4 is preferably a silica fiber or a glass fiber, more preferably a silica fiber. In this embodiment, a silica fiber is used as the anionic adsorbent 4. The anionic adsorbent 4 may also be silica particles or a silica porous body.

In the adsorption step, the extraction solution obtained in the extraction step and containing the nucleic acid is fed to the collection section 3 from the upstream-side flow path 2a to bring the extraction solution into contact with the anionic adsorbent 4. By carrying out the adsorption step, the nucleic acid contained in the extraction solution can be adsorbed onto the anionic adsorbent 4.

(Washing Step)

Subsequently, the nucleic acid isolation method according to the first embodiment of the present invention includes a step of bringing a washing solution into contact with the anionic adsorbent. The washing solution contains a basic compound and has a pH value equal to or less than the pKa value of a conjugate acid of the basic compound. This step is referred to as a "washing step" and is explained hereinbelow.

In the nucleic acid isolation method according to the first embodiment of the present invention, the washing step is a step of feeding the washing solution from the upstream-side flow path 2a to the collection section 3 to bring the washing solution into contact with the anionic adsorbent 4. By the washing step, a crosslinked structure is formed between the nucleic acid and the anionic adsorbent 4 through the basic compound contained in the washing solution. Furthermore, by the washing step, contaminants adsorbed on the anionic adsorbent 4 can be washed off.

Basic Compound;

The washing solution contains a basic compound and has a pH value equal to or less than the pKa value of a conjugate acid of the basic compound. Therefore, in the washing solution, some of molecules of the basic compound exist as positively-charged cations. In this case, the nucleic acid can be adsorbed firmly onto the anionic adsorbent 4 by allowing the cations to form a crosslinking structure between the anionic adsorbent 4 and the nucleic acid (which is generally negatively charged) as shown in FIG. 3(a). Furthermore, because the basic compound is dissolved in the form of a cation in the washing solution, a crosslinked structure can be formed between the basic compound and the nucleic acid uniformly, and thereby the collection rate of the nucleic acid can be more likely to be improved.

The term "basic compound" as used herein refers to a compound which can accept a proton ($H^+$) in accordance with the Bronsted-Lowry definition, or an ion of the compound. When the basic compound can be ionized in multiple stages, the pKa value of a conjugate acid of the basic compound means an acid dissociation constant $pKa1$ of a conjugate acid of the basic compound when the basic compound is ionized in one stage.

The basic compound may be any one of a monomer, an oligomer and a polymer, or may be a combination thereof. When the washing solution is used in a microfluidic device, the basic compound is preferably a monomer having a low thickening effect. The weight average molecular weight of the monomer is preferably 700 or less. The weight average molecular weight of the oligomer is preferably less than 10,000. The weight average molecular weight of the polymer is preferably 10,000 or more.

With respect to the basic compound, the pKa value of a conjugate acid thereof is preferably 4 or more, more preferably 4.5 or more, and is preferably 6 or less, more preferably 5.5 or less. When the pKa value of the conjugate acid falls within the above-mentioned range, it becomes possible to extract the nucleic acid more efficiently.

The basic compound may be a monovalent base or a bivalent base, and is preferably a base having a valency of 2 or more. In this case, it becomes possible to adsorb the nucleic acid more firmly.

The basic compound preferably has an amino group. When the basic compound is a monomer having an amino group, examples of the monomer include a polyamine-based monomer, a radical-reactive amine monomer, a polycondensable amine monomer, an amino sugar, and a pyridine compound. These monomers may be used singly, or two or more of them may be used in combination.

Examples of the polyamine-based monomer include melamine, piperazine, 1,4-diazabicyclo[2.2.2]octane (DABCO), methoxyamine, dime thylhydroxyamine, trisdimethylaminoethylamine, diethylenetriamine, methylaminoacetonitrile, diethylaminoacetonitrile, nitrourea, aminoethylmorpholine, hexamethylenetetramine, triethylenediamine, dimethylhydroxyamine, isoquinoline, histidine, benzimidazole, biguanide, spermine, spermidine and putrescine.

Examples of the radical-reactive amine monomer include allylamine and acrylamine.

An example of the polycondensable amine monomer is polyethyleneimine.

Examples of the amino sugar include acarbose, N-acetylneuraminic acid, phosphoribosylamine and glucosamine.

Examples of the pyridine compound include pyridine, nicotinic acid, nicotinic acid amide, isoniazid, nicotine, brucine and vitamin B6.

When the basic compound is a polymer having an amino group, examples of the polymer include a long-chain polyamine (LCPA), an amino-sugar-based polysaccharide, a pyridine-based polymer, and a polymer having a repeating structural unit derived from any one of the above-mentioned monomers. These polymers may be used singly, or two or more of them may be used in combination.

Examples of the long-chain polyamine (LCPA) include silaffin and silacidin.

An example of the amino-sugar-based polysaccharide is chitosan.

Examples of the pyridine-based polymer include polypyridine and a polyalkylpyridinium.

As the oligomer, an oligomer having a repeating structural unit derived from any one of the above-mentioned monomers can be used for example.

Among these compounds, from the viewpoint that the nucleic acid can be supported on the anionic adsorbent 4 more reliably, the basic compound is preferably melamine, piperazine or 1,4-diazabicyclo[2.2.2]octane (DABCO), more preferably melamine. The pKa value of melamine in an aqueous solution is 5.0 to 5.1. Therefore, in an aqueous solution having a pH value of 7, the basic compound becomes in a non-ionized state as shown in formula (1) below. In an aqueous solution having a pH value of 4, some or all of molecules of the basic compound are ionized and are converted into cations each having a valency of 1 to 3, as shown in formulas (2) to (4). Therefore, melamine can be used suitably as a compound having a pKa value of 4 or more and 6 or less.

[Chemical 1]

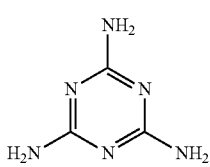

Formula (1)

[Chemical 2]

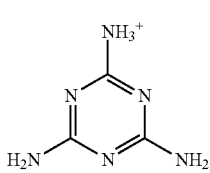

Formula (2)

[Chemical 3]

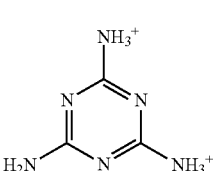

Formula (3)

[Chemical 4]

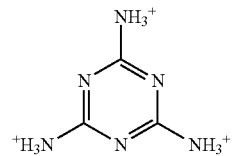

Formula (4)

The pH value of the washing solution is not particularly limited, as long as the pH value is equal to or less than the pKa value. From the viewpoint of more reliably supporting the nucleic acid on the anionic adsorbent 4 through the basic compound, the difference between the pKa value and the pH value of the washing solution is preferably 1 or more, more preferably 2 or more. The upper limit of the difference between the pKa value and the pH value of the washing solution is not particularly limited, and can be, for example, 5.

The concentration of the basic compound in the washing solution is not particularly limited, and is preferably 10 mmol/L or more, and is preferably 1 mol/L or less, more preferably 500 mmol/L or less. When the concentration of the basic compound falls within the above-mentioned range, it becomes possible to support the nucleic acid on the anionic adsorbent 4 through the basic compound more reliably.

In the present invention, when the anionic adsorbent 4 has the form of a fiber or a porous body, it is preferred that the compound is a monomer. In this case, it becomes possible to achieve the contact of the anionic adsorbent 4 with the compound with higher efficiency.

When the anionic adsorbent 4 has the form of particles, it is preferred that the amine-based compound is a polymer. In this case, it becomes possible to achieve the contact ow the anionic adsorbent 4 with the amine-based compound with higher efficiency.

(Collection Step)

Subsequently, the nucleic acid isolation method according to the first embodiment of the present invention includes a step of bringing a collection solution into contact with the anionic adsorbent. This step is referred to as a "collection step" and is explained hereinbelow.

In the nucleic acid isolation method according to the first embodiment of the present invention, the collection step is a step of feeding the collection solution from the upstream-side flow path 2a to the collection section 3 to bring the collection solution into contact with the anionic adsorbent 4. In this regard, the pH value of the collection solution is more than the pKa value of the basic compound, and therefore most of molecules of the basic compound become in a non-ionized state. Therefore, when the collection solution is fed to the collection section 3, ionic bonds formed between the negatively charged nucleic acid and the basic compound and between the anionic adsorbent 4 and the basic compound are broken as shown in FIG. 3(b). Therefore, by feeding the collection solution to the collection section 3, the nucleic acid can be isolated from the anionic adsorbent 4 and can be collected from a collection port 7. The difference between the pH value of the collection solution and the pKa value is preferably 1 or more, more preferably 2 or more. The upper limit of the difference between the pH value of the collection solution and the pKa value is not particularly limited, and can be, for example, 3.

As mentioned above, in the nucleic acid isolation method according to this embodiment, the nucleic acid can be adsorbed onto the anionic adsorbent 4 firmly by using the extraction solution and the washing solution containing the basic compound and having a pH value equal to or less than the pKa value of a conjugate acid of the basic compound. The nucleic acid can also be isolated from the anionic adsorbent 4 and collected by using the collection solution having a pH value equal to or more than the pKa value of a conjugate acid of the basic compound. Accordingly, in the nucleic acid isolation method of this embodiment, the nucleic acid can be collected more easily using the extraction solution, the washing solution and the collection solution without the need to use an alcohol.

The pH value of the collection solution is only required to be equal to or more than the pKa value of a conjugate acid of the basic compound, and the collection solution may be neutral. Therefore, because the nucleic acid can be isolated and collected with a neutral collection solution, the inhibition of a reaction, e.g., an enzymatic reaction, can also be prevented in a test or an analysis in a later step.

(Other Step)

The nucleic acid isolation method according to the first embodiment of the present invention may further include a step other than the above-mentioned steps, if necessary. For example, the method may further include other step, e.g., a drying step, subsequent to the adsorption step.

(Nucleic Acid Isolation Method According to Second Embodiment)

The nucleic acid isolation method according to a second embodiment of the present invention comprises the steps of:
mixing a specimen containing a nucleic acid with an extraction solution to disperse the nucleic acid in the extraction solution;
bringing the extraction solution containing the nucleic acid into contact with an anionic adsorbent; and
bringing a collection solution into contact with the anionic adsorbent. The extraction solution contains a protein denaturant and a basic compound, and has a pH value equal to or less than a pKa value of a conjugate acid of the basic compound. The collection solution has a pH value equal to or more than the pKa value of the conjugate acid of the basic compound.

The nucleic acid isolation method according to the second embodiment is different from the nucleic acid isolation method according to the first embodiment in that the extraction solution contains the basic compound and has a pH value equal to or less than the pKa value of a conjugate acid of the basic compound.

In the nucleic acid isolation method according to the second embodiment, the same steps as those employed in the nucleic acid isolation method according to the first embodiment can be employed, except the above-mentioned point. In the nucleic acid isolation method according to the second embodiment, it is not necessarily required to provide the washing step. When the washing step is not provided in the nucleic acid isolation method according to the second embodiment, it becomes possible to isolate the nucleic acid more easily and more rapidly. On the other hand, when the washing step is provided in the nucleic acid isolation method according to the second embodiment of the present invention, it becomes possible to isolate the nucleic acid that contains a smaller amount of contaminants. In the nucleic acid isolation method according to the second embodiment, the washing solution is only required to have a pH value equal to or less than the pKa value of the basic compound. In this case, the contaminants or the like can be washed off while keeping the nucleic acid adsorbed on the anionic adsorbent.

According to the nucleic acid isolation method of the second embodiment of the present invention, the nucleic acid can be collected more easily using the extraction solution and the collection solution without the need to use an alcohol.

[Nucleic Acid Isolation Kit]

The present invention also relates to a nucleic acid isolation kit.

(Nucleic Acid Isolation Kit According to First Embodiment)

The nucleic acid isolation kit according to a first embodiment of the present invention comprises an extraction solution, a washing solution, a collection solution and an anionic adsorbent. The extraction solution contains a protein denaturant. The washing solution contains a basic compound and has a pH value equal to or less than a pKa value of a conjugate acid of the basic compound. The collection solution has a pH value equal to or more than the pKa value of the conjugate acid of the basic compound. According to the nucleic acid isolation kit of the first embodiment, by employing the nucleic acid isolation method according to the first embodiment as mentioned above, the nucleic acid can be isolated more easily using the extraction solution, the washing solution and the collection solution without the need to use an alcohol.

In the nucleic acid isolation kit according to the first embodiment, as the extraction solution, the washing solution, the collection solution and the anionic adsorbent, the same ones as those described in the nucleic acid isolation method according to the first embodiment as mentioned above can be used.

(Nucleic Acid Isolation Kit According to Second Embodiment)

The nucleic acid isolation kit according to a second embodiment of the present invention comprises an extraction solution, a collection solution and an anionic adsorbent. The extraction solution contains a protein denaturant and a basic compound, and has a pH value equal to or less than the pKa value of a conjugate acid of the basic compound. The collection solution has a pH value equal to or more than the pKa value of the conjugate acid of the basic compound. According to the nucleic acid isolation kit of the second embodiment, by employing the nucleic acid isolation method according to the second embodiment as mentioned above, the nucleic acid can be isolated more easily using the extraction solution and the collection solution without the need to use an alcohol.

In the nucleic acid isolation kit according to the second embodiment, as the extraction solution, the collection solution and the anionic adsorbent, the same ones as those described in the nucleic acid isolation method according to the second embodiment as mentioned above can be used. The nucleic acid isolation kit according to the second embodiment may further include a washing solution. As the washing solution, the same one as described in the nucleic acid isolation method according to the second embodiment can be used.

In each of the nucleic acid isolation kits according to the first and second embodiments, it is preferred that the extraction solution, the washing solution and the collection solution are contained in a first container, a second container and a third container, respectively. It is also preferred that the anionic adsorbent is held in the inside of a column of which an upper part and a lower part are opened. Furthermore, it is also preferred that the first container, the second container, the third container and the column are provided in such a form that these items are contained in a box. Furthermore, it is also preferred that a package insert for explaining the usage and the like of the nucleic acid isolation kit is also contained in the box.

[Test Chip]

The present invention also relates to a test chip.

(Test chip according to first embodiment)

The test chip according to a first embodiment of the present invention comprises:

an extraction solution holding section in which an extraction solution containing a nucleic acid is held;
a washing solution holding section in which a washing solution is held;
a collection solution holding section in which a collection solution is held;
a collection section containing an anionic adsorbent; and
a nucleic acid analysis section. The extraction solution contains a protein denaturant. The washing solution contains a basic compound and has a pH value equal to or less than a pKa value of a conjugate acid of the basic compound. The collection solution has a pH value equal to or more than the pKa value of the conjugate acid of the basic compound.

In the test chip according to the first embodiment, as the extraction solution, the washing solution, the collection solution and the anionic adsorbent, the same ones as those described in the nucleic acid isolation method according to the first embodiment as mentioned above can be used.

FIG. 4 is a schematic view showing one example of a flow path structure in the test chip according to the first embodiment of the present invention. FIG. 5 is a front sectional view of a part taken along line B-B in FIG. 4.

In FIGS. 4 and 5, the test chip 11 comprises a substrate 12 and a sealing sheet 13. The substrate 12 is not particularly limited. In this embodiment, the substrate 12 has a rectangular sheet-like shape. The substrate 12 has a first surface 12a that is located on the side of the sealing sheet 13 and a second surface 12b that is opposed to the first surface 12a. In the test chip 11, a plurality of groove parts provided on the first surface 12a side are sealed with the sealing sheet 13 to form first to fifth flow paths 24A to 24E and a collection section 28. In the collection section 28, the anionic adsorbent 14 is provided.

As the material constituting the substrate 12, an appropriate material such as a synthetic resin can be used. An example of the material constituting the sealing sheet 13 is a resin film.

Upstream ends of the first to third flow paths 24A to 24C are respectively connected to micro pumps 23A to 23C, and downstream ends thereof are connected to the collection section 28. In the middle of the first flow path 24A, an extraction solution holding section 25 is provided. In the middle of the second flow path 24B, a washing solution holding section 26 is provided. In the middle of the third flow path 24C, a collection solution holding section 27 is provided.

Each of the micro pumps 23A to 23C is not particularly limited, and an example thereof is a light gas generation tape. The term "light gas generation tape" refers to a tape which can generate a gas upon being irradiated with light.

An upstream end of the fourth flow path 24D is connected to the collection section 28, and a downstream end thereof is connected to a waste fluid section 29. In the middle of the fourth flow path 24D, a valve section 21A is provided so as to open and close the fourth flow path 24D.

An upstream end of the fifth flow path 24E is connected to the collection section 28, and a downstream end thereof is connected to a nucleic acid analysis section 22. In the middle of the fifth flow path 24E, a valve section 21B is provided so as to open and close the fifth flow path 24E.

Nucleic Acid Analysis Section;

After the nucleic acid is isolated with the collection solution, the analysis of the nucleic acid is carried out in the nucleic acid analysis section 22. The method for analyzing the nucleic acid which is carried out in the nucleic acid analysis section 22 is not particularly limited. An example of the method is PCR (Polymerase Chain Reaction). In order to achieve the isolation and analysis of the nucleic acid rapidly, it is preferred that a reagent to be used for the analysis of the nucleic acid is provided in the nucleic acid analysis section 22 previously. Examples of the reagent to be used for the analysis of the nucleic acid include a primer and a polymerase for use in PCR.

Next, one example of the nucleic acid isolation method using the test chip according to the first embodiment is explained hereinbelow.

Firstly, in the outside of the system of the test chip 11, the extraction solution and the specimen containing the nucleic acid as mentioned above are mixed together to prepare the extraction solution containing the nucleic acid (extraction step). Subsequently, the extraction solution containing the nucleic acid is injected into the extraction solution holding section 25 through an injection port (not shown). Subsequently, a micro pump 23A is driven to bring the extraction solution injected to the extraction solution holding section 25 into contact with the anionic adsorbent 14 in the collection section 28 and is then fed to the waste fluid section 29 (adsorption step). At this time, the valve section 21A is opened and the valve section 21B is closed. Subsequently, a micro pump 23B is driven to bring the washing solution held in the washing solution holding section 26 into contact with the anionic adsorbent 14 in the collection section 28 and is then fed to the waste fluid section 29 (washing step). Subsequently, the valve section 21A is closed and the valve section 21B is opened. Subsequently, a micro pump 23C is driven to bring the collection solution held in the collected solution holding section 27 into contact with the anionic adsorbent 14 to isolate the nucleic acid, and then the collection solution containing the nucleic acid is fed to the nucleic acid analysis section 22 (collection step).

According to the test chip of the first embodiment, the nucleic acid can be isolated and analyzed more easily using the extraction solution, the washing solution and the collection solution without the need to use an alcohol by employing the nucleic acid isolation method according to the first embodiment.

The configuration of the test chip according to the first embodiment and the nucleic acid isolation method using the test chip are just one example, and the configuration and the nucleic acid isolation method may be modified appropriately within the scope in which the object of the present invention can be achieved.

(Test Chip According to Second Embodiment)

The test chip according to a second embodiment of the present invention comprises:

an extraction solution holding section in which an extraction solution containing a nucleic acid is held;
a collection solution holding section in which a collection solution is held;
a collection section containing an anionic adsorbent; and
a nucleic acid analysis section. The extraction solution contains a protein denaturant and a basic compound, and has a pH value equal to or less than a pKa value of a conjugate acid of the basic compound. The collection solution has a pH value equal to or more than the pKa value of the conjugate acid of the basic compound.

In the test chip according to the second embodiment, as the extraction solution, the collection solution and the anionic adsorbent, the same ones as those described in the nucleic acid isolation method according to the second embodiment as mentioned above can be used.

The test chip according to the second embodiment may further include a washing solution holding section in which a washing solution is held. As the washing solution, the same one as described in the nucleic acid isolation method according to the second embodiment as mentioned above can be used.

As the test chip according to the second embodiment, a test chip having the same configuration as that of the test chip according to the first embodiment can be used. In the test chip according to the second embodiment, it is not necessarily required to provide the washing solution holding section. When the washing solution holding section is not provided in the test chip according to the second embodiment, it becomes possible to isolate the nucleic acid more easily and more rapidly. When the washing solution holding section is provided in the test chip according to the second embodiment, it becomes possible to isolate the nucleic acid that contains a smaller amount of contaminants.

As the nucleic acid isolation method using the test chip according to the second embodiment, the same method as the nucleic acid isolation method using the test chip according to the first embodiment can be employed. In the nucleic acid isolation method using the test chip according to the second embodiment, it is not necessarily required to provide the washing step. In the test chip according to the second embodiment, when the washing step is not provided, it becomes possible to isolate the nucleic acid more easily and more rapidly. On the other hand, in the test chip according to the second embodiment, when the washing step is provided, it becomes possible to isolate the nucleic acid that contains a smaller amount of contaminants.

According to the test chip of the second embodiment, the nucleic acid can be isolated and analyzed more easily using the extraction solution, the washing solution and the collection solution without the need to use an alcohol by employing the nucleic acid isolation method according to the second embodiment as mentioned above.

The configuration of the test chip according to the second embodiment and the nucleic acid isolation method using the test chip are just one example, and the configuration and the nucleic acid isolation method may be modified appropriately within the scope in which the object of the present invention can be achieved.

EXAMPLES

Hereinbelow, the present invention is described clearly with reference to specific examples and comparative examples of the present invention. However, the present invention is not limited to the following examples.

Example 1

In Example 1, a chip 1 shown in FIGS. 1 and 2 was produced as follows.

A cycloolefin polymer was used as a material constituting a substrate 5, and the cycloolefin polymer was injection-molded to produce a substrate 5 having a depressed part 5b. A sealing tape was used as a cover member 6, and the depressed part 5b in the substrate 5 was closed with the sealing tape. In this manner, the chip 1 was produced. In a collection section 3, silica fibers ("GF/D" manufactured by GE Healthcare, 2 mmφ, thickness 0.8 mm) was placed as an anionic adsorbent 4. The width and depth of a flow path 2 were 0.8 mm and 0.5 mm, respectively.

The collection rate of RNA was measured using the chip 1.

Isolation of RNA;

In the outside of the system of the chip 1, a virus (FluA H1N1 manufactured by ATCC; 5000 copies) was added to an extraction solution (500 µL) having the composition shown in Table 1 to produce an extraction solution having a nucleic acid (RNA) dispersed therein. A co-precipitant (polyadenine) shown in Table 1 was added in an amount of 3 µg per 500 µL of the extraction solution. Subsequently, the extraction solution (150 µL) containing the RNA was fed to a collection section 3 to allow the RNA to be adsorbed on the silica fibers. After the feeding of the extraction solution containing the RNA, a washing solution (200 µL) shown in Table 1 was fed to the collection section 3 to wash the silica fibers.

Subsequently, Tris-HCl Buffer (50 mM, pH 8.5) (30 µL) which served as a collection solution was fed to the collection section 3 to isolate the RNA supported on the collection section 3, and the RNA was then collected.

(Calculation of RNA Collection Rate)

Subsequently, an aliquot (2 µL) was removed from the collection solution in which the nucleic acid was collected, and then a PCR reaction solution was prepared using Taq-Path qPCR and RT-qPCR Master Mixes (manufactured by Thermofisher). As a PCR primer, a PDM 2009 H1N1 detection primer (InfA, Universal Influenza a Primer) manufactured by Biosearch Technologies, Inc. was used.

As standards, PCR reaction solutions in each of which a solution (2 µL) prepared by extracting and purifying the same virus using QIAamp Viral RNA Mini Kit (manufactured by QIAGEN) were also prepared (the concentration of the nucleic acid: 4 kinds of standards, i.e., 100,000 copies/µL, 50,000 copies/µL, 5,000 copies/µL, and 500 copies/µL).

Subsequently, each of the PCR reaction solution prepared from the collection solution and the standard PCR reaction solutions was amplified using a thermal cycler "LightCycler (manufactured by Roche)". For the amplification, heating was carried out at 95° C. for 20 seconds, and then 45 cycles of 95° C. for 3 seconds and 60° C. for 5 seconds were carried out.

After the amplification, the RNA collection rate (nucleic acid collection rate) was calculated from the amount of the nucleic acid which was automatically calculated by Light-Cycler on the basis of the standards, in accordance with the following equation.

Nucleic acid collection rate (%) =

{((amount of nucleic acid calculated by $LightCycler$) ×

(volume of collected solution)/2) × 100}/5,000

Examples 2 to 7

The same procedure as in Example 1 was carried out, except that the types and addition amounts of the compounds contained in the extraction solution and the washing solution were changed to those shown in Table 1 and that the washing step was not provided in Example 6. In this manner, RNA collection rates were determined. The results are shown in Table 1. The pKa value of a conjugate acid of DABCO in Example 2 was 4.2, and the pKa value of a conjugate acid of piperazine in Example 3 was 5.7. In Table 1, the unit "mol/L" is expressed in "M".

Comparative Example 1

In Comparative Example 1, the RNA collection rate was determined in the same manner as in Example 1, except that ethanol (200 μL) was used as the washing solution.

Comparative Example 2

In Comparative Example 2, the RNA collection rate was determined in the same manner as in Example 1, except that the washing solution was not fed after the feeding of the extraction solution containing the RNA.
The results are shown in Table 1.

TABLE 1

| | | Example 1 | Example 2 | Example 3 | Example 4 | Example 5 | Example 6 | Example 7 | Comparative Example 1 | Comparative Example 2 |
|---|---|---|---|---|---|---|---|---|---|---|
| Extraction solution | Urea | 4M | 4M | 4M | 4M | 4M | 4M | 4M | 4M | 4M |
| | Guanidine hydrochloride | 4M | 4M | 4M | 4M | | | | 4M | 4M |
| | Calcium chloride | 2M | 2M | 2M | 2M | | | | 2M | 2M |
| | Glycine | | | | 1M | 1M | | | | |
| | Melamine (pKa = 5.0-5.1) | | | | | | 50 mM | 50 mM | | |
| | Co-precipitant (polyadenine) | 3 μg | 3 μg | 3 μg | 3 μg | 3 μg | 3 μg | 3 μg | 3 μg | 3 μg |
| | pH | 7 | 7 | 7 | 7 | 4 | 4 | 4 | 7 | 7 |
| Washing solution | Melamine (pKa = 5.0-5.1) | 50 mM | | | 50 mM | 50 mM | Without washing | 50 mM | Washed with ethanol | Without washing |
| | DABCO (pKa = 4.2) | | 50 mM | | | | | | | |
| | Piperazine (pKa = 5.7) | | | 50 mM | | | | | | |
| | pH | 4 | 4 | 4 | 4 | 4 | | 4 | | |
| Collection solution | Tris-HCl Buffer (50 mM, pH 8.5) | ○ | ○ | ○ | ○ | ○ | ○ | ○ | ○ | ○ |
| Evaluation | RNA collection rate (%) | 70 | 60 | 55 | 75 | 70 | 60 | 65 | 0 | 0 |

INDUSTRIAL APPLICABILITY

According to the present invention, it becomes possible to provide a nucleic acid isolation method, a nucleic acid isolation kit and a test chip whereby it becomes possible to extract a nucleic acid in a simple manner without the need to use an alcohol.

EXPLANATION OF SYMBOLS

1: chip
2: flow path
2a: upstream-side flow path
2b: downstream-side flow path
3: collection section
4: anionic adsorbent
5: substrate
5a: main surface
5b: depressed part
6: cover member
7: collection port
11: test chip
12: substrate
12a, 12b: first and second surfaces
13: sealing sheet
14: anionic adsorbent
21A, 21B: first and second valve sections
22: nucleic acid analysis section
23A~23C: micro pumps
24A~24E: first to fifth flow paths
25: extraction solution holding section
26: washing solution holding section
27: collected solution holding section
28: collection section
29: waste fluid section

The invention claimed is:

1. A nucleic acid isolation method, comprising steps of:
mixing a specimen containing a nucleic acid with an extraction solution to disperse the nucleic acid in the extraction solution;
bringing the extraction solution containing the nucleic acid into contact with an anionic adsorbent;
bringing a washing solution into contact with the anionic adsorbent; and
bringing a collection solution into contact with the anionic adsorbent,
the extraction solution containing a protein denaturant,
the washing solution containing a basic compound and having a pH value equal to or less than a pKa value of a conjugate acid of the basic compound,
the basic compound containing at least one selected from the group consisting of melamine, and 1,4-diazabicyclo [2.2.2]octane, and
the collection solution having a pH value equal to or more than the pKa value of the conjugate acid of the basic compound.

2. The nucleic acid isolation method according to claim 1, wherein the extraction solution further contains a metal cation having a valency of 2 or more.

3. A nucleic acid isolation method, comprising steps of:
mixing a specimen containing a nucleic acid with an extraction solution to disperse the nucleic acid in the extraction solution;
bringing the extraction solution containing the nucleic acid into contact with an anionic adsorbent; and
bringing a collection solution into contact with the anionic adsorbent, the extraction solution containing a protein denaturant and a basic compound, and having a pH value equal to or less than a pKa value of a conjugate acid of the basic compound, the basic compound containing at least one selected from the group consisting of melamine, and 1,4-diazabicyclo[2.2.2]octane, and the collection solution having a pH value equal to or more than the pKa value of the conjugate acid of the basic compound.

4. The nucleic acid isolation method according to claim 1, wherein the pKa value of the conjugate acid of the basic compound is 4 or more and 6 or less.

5. The nucleic acid isolation method according to claim 1, wherein the basic compound contains melamine.

6. The nucleic acid isolation method according to claim 1, wherein the extraction solution further contains a zwitterionic compound.

7. The nucleic acid isolation method according to claim 1, wherein a step of bringing a solution containing an alcohol into contact with the anionic adsorbent is not comprised.

\* \* \* \* \*